US010470734B2

(12) United States Patent
Madabhushi et al.

(10) Patent No.: US 10,470,734 B2
(45) Date of Patent: *Nov. 12, 2019

(54) CHARACTERIZING LUNG NODULE RISK WITH QUANTITATIVE NODULE AND PERINODULAR RADIOMICS

(71) Applicant: Case Western Reserve University, Cleveland, OH (US)

(72) Inventors: Anant Madabhushi, Shaker Heights, OH (US); Mahdi Orooji, Cleveland, OH (US); Mirabela Rusu, Cleveland, OH (US); Philip Linden, Pepper Pike, OH (US); Robert Gilkeson, Cleveland Heights, OH (US); Nathaniel Mason Braman, Cleveland, OH (US); Mehdi Alilou, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,498

(22) Filed: Jul. 24, 2018

(65) Prior Publication Data

US 2018/0353149 A1    Dec. 13, 2018

Related U.S. Application Data

(63) Continuation of application No. 15/226,148, filed on Aug. 2, 2016, now Pat. No. 10,064,594.

(Continued)

(51) Int. Cl.
*A61B 6/00* (2006.01)
*G06T 11/00* (2006.01)
(Continued)

(52) U.S. Cl.
CPC ............. *A61B 6/5217* (2013.01); *A61B 5/055* (2013.01); *A61B 5/08* (2013.01); *A61B 5/4312* (2013.01);
(Continued)

(58) Field of Classification Search
CPC .......... A61B 10/0041; A61B 2034/105; A61B 5/055; A61B 5/08; A61B 5/4312;
(Continued)

(56) References Cited

U.S. PATENT DOCUMENTS 9,092,691 B1 * 7/2015 Beaumont ............. G06T 7/0014
10,004,471 B2   6/2018 Madabhushi et al.
(Continued)

OTHER PUBLICATIONS

Final Office Action dated Dec. 27, 2018 in connection with U.S. Appl. No. 15/937,105.
(Continued)

*Primary Examiner* — Aklilu K Woldermariam
(74) *Attorney, Agent, or Firm* — Eschweiler & Potashnik, LLC

(57) ABSTRACT

Embodiments associated with classifying a region of tissue using features extracted from nodules and surrounding structures. One example apparatus includes a feature extraction circuit configured to automatically extract a first set of quantitative features from a nodule represented in at least one CT image, and automatically extract a second set of quantitative features from the lung parenchyma region immediately surrounding the nodule represented in the at least one CT image; a feature selection circuit configured to select an optimally predictive feature set from the first set of quantitative features and the second set of quantitative features; and a training circuit configured to train a classifier using the optimally predictive feature set to assign malignancy risk to a lung nodule represented in a CT image of a region of tissue demonstrating lung nodules. A prognosis or (Continued)

treatment plan may be provided based on the malignancy risk.

19 Claims, 10 Drawing Sheets

Related U.S. Application Data

(60) Provisional application No. 62/201,837, filed on Aug. 6, 2015.

(51) Int. Cl.

| | | |
|---|---|---|
| G06K 9/46 | (2006.01) | |
| G06K 9/00 | (2006.01) | |
| A61B 6/03 | (2006.01) | |
| A61B 5/08 | (2006.01) | |
| A61B 5/055 | (2006.01) | |
| A61B 5/00 | (2006.01) | |
| A61B 10/00 | (2006.01) | |
| G01R 33/56 | (2006.01) | |
| G06K 9/62 | (2006.01) | |
| G06T 7/00 | (2017.01) | |
| G06T 7/40 | (2017.01) | |
| G06T 7/11 | (2017.01) | |
| G06T 7/136 | (2017.01) | |
| G06T 7/62 | (2017.01) | |
| A61B 34/10 | (2016.01) | |
| A61B 6/12 | (2006.01) | |

(52) U.S. Cl.
CPC ............ *A61B 5/7267* (2013.01); *A61B 6/032* (2013.01); *A61B 10/0041* (2013.01); *G01R 33/5601* (2013.01); *G06K 9/00147* (2013.01); *G06K 9/46* (2013.01); *G06K 9/4604* (2013.01); *G06K 9/6267* (2013.01); *G06T 7/0012* (2013.01); *G06T 7/11* (2017.01); *G06T 7/136* (2017.01); *G06T 7/40* (2013.01); *G06T 7/62* (2017.01); *G06T 11/003* (2013.01); *G06T 11/008* (2013.01); *A61B 6/12* (2013.01); *A61B 2034/105* (2016.02); *G01R 33/5608* (2013.01); *G06K 9/00* (2013.01); *G06K 9/6269* (2013.01); *G06T 2207/10081* (2013.01); *G06T 2207/10096* (2013.01); *G06T 2207/20081* (2013.01); *G06T 2207/30064* (2013.01); *G06T 2207/30068* (2013.01); *G06T 2207/30101* (2013.01); *G06T 2211/404* (2013.01)

(58) Field of Classification Search
CPC ......... A61B 5/7267; A61B 6/032; A61B 6/12; A61B 6/5217; A61B 6/50; A61B 5/413; A61B 5/415; A61B 5/417; A61B 5/418; A61B 5/4504; A61B 6/027; A61B 6/4085; A61B 6/481; A61B 6/504; A61B 6/508; G06T 7/0085; G06T 2207/10081; G06T 7/0012; G06T 11/008; G06T 15/08; G06T 17/10; G06T 2200/04; G06T 2207/30064; G06T 7/155; G06T 7/62; G06T 7/136; G06T 11/003; G06T 2207/10096; G06T 2207/20081; G06T 2207/20144; G06T 2207/30061; G06T 2207/30101; G06T 7/0081; G06T 7/40; G06T 7/604; G06T 2207/20141; G06T 2207/30068; G06T 2207/30096; G06T 5/002; G06T 5/005; G06T 5/30; G06T 7/11; G06T 2211/404; C12Q 1/6886; C12Q 2600/158; C12Q 2600/112; C12Q 2600/178; C12Q 2600/106; C12Q 2600/156; G01N 33/574; G01N 33/57407; G01N 2333/70596; G01N 33/5011; G01N 33/57423; G06F 19/20; G06K 9/00147; G06K 9/46; G06K 9/4604; G06K 9/6267; G06K 9/00; G06K 9/6269; G06Q 99/00; A61K 31/69; A61K 45/06; G01R 33/5601; G01R 33/5608
USPC ............... 382/128, 129, 130, 131, 132, 154; 600/439, 567, 566
See application file for complete search history.

(56) References Cited

U.S. PATENT DOCUMENTS

| | | | |
|---|---|---|---|
| 2003/0095692 A1* | 5/2003 | Mundy | A61B 6/00 382/128 |
| 2004/0252870 A1* | 12/2004 | Reeves | G06T 7/0012 382/128 |
| 2005/0207630 A1* | 9/2005 | Chan | A61B 6/466 382/131 |
| 2007/0019846 A1 | 1/2007 | Bullitt | |
| 2007/0081712 A1* | 4/2007 | Huang | G06T 7/33 382/128 |
| 2008/0002870 A1* | 1/2008 | Farag | G06K 9/0014 382/128 |
| 2008/0205717 A1* | 8/2008 | Reeves | G06T 7/0012 382/128 |
| 2009/0005693 A1* | 1/2009 | Brauner | A61B 6/508 600/481 |
| 2010/0111386 A1* | 5/2010 | El-Baz | G06T 7/0016 382/128 |
| 2010/0323903 A1* | 12/2010 | Rosenwald | C12Q 1/6886 506/7 |
| 2012/0150048 A1* | 6/2012 | Kang | A61B 6/508 600/481 |
| 2013/0217956 A1* | 8/2013 | Thompson | A61B 17/12022 600/37 |
| 2013/0225662 A1* | 8/2013 | Kennedy | C12Q 1/6886 514/44 R |
| 2013/0259345 A1* | 10/2013 | El-Baz | G06T 7/0012 382/131 |
| 2016/0110632 A1* | 4/2016 | Kiraly | G06K 9/66 382/128 |
| 2016/0155225 A1* | 6/2016 | Madabhushi | G06T 7/0012 382/131 |
| 2016/0239956 A1 | 8/2016 | Kang | |
| 2016/0260224 A1* | 9/2016 | Ward | G06T 7/0012 |
| 2017/0035381 A1 | 2/2017 | Madabhushi | |
| 2017/0039737 A1* | 2/2017 | Madabhushi | A61B 5/7267 |

OTHER PUBLICATIONS

Notice of Allowance dated Apr. 16, 2019 for U.S. Appl. No. 15/937,105.

Non-Final Office Action dated Aug. 29, 2018 in connection with U.S. Appl. No. 15/937,105.

Fraioli, et al. "CAD (Computed-Aided Detection) and CADx (Computer Aided Diagnosis) Systems in Identifying and Characterising Lung Nodules on Chest CT: Overview of Research, Developments and New Prospects." Radiol Med (2010) 115:385-402, published Jan. 15, 2010.

Awai, et al. "Pulmonary Nodules: Estimation of Malignancy at Thin-Section Helical CT—Effect of Computer-aided Diagnosis on Performance of Radiologists." Radiology: vol. 239: No. 1, Apr. 2006.

Ko, et al. "Lung Adenocarcinoma: Correlation of Quantitative CT Findings with Pathologic Findings." Radiology: vol. 280: No. 3, Sep. 2016.

Aoyama, et al. "Computerized Scheme for Determination of the Likelihood Measure of Malignancy for Pulmonary Nodules on Low-Dose CT Images." Med. Phys. 30 (3), Mar. 2003.

(56) References Cited

OTHER PUBLICATIONS

Notice of Allowance dated May 2, 2018 for U.S. Appl. No. 15/226,148.
Non-Final Office Action dated Oct. 30, 2017 for U.S. Appl. No. 15/226,148.
Non-Final Office Action dated Oct. 30, 2017 for U.S. Appl. No. 15/226,124.
Notice of Allowance dated Oct. 30, 2017 for U.S. Appl. No. 15/226,124.
U.S. Appl. No. 15/937,105, filed Mar. 27, 2018.
U.S. Appl. No. 15/883,649, filed Jan. 30, 2018.
Notice of Allowance dated Jul. 31, 2019 for U.S. Appl. No. 15/883,649.

* cited by examiner

CHARACTERIZING LUNG NODULE RISK WITH QUANTITATIVE NODULE AND PERINODULAR RADIOMICS

CROSS REFERENCE TO RELATED APPLICATIONS

This Application is a Continuation of U.S. application Ser. No. 15/226,148 filed on Aug. 2, 2016, which claims priority to U.S. Provisional Application No. 62/201,837 filed on Aug. 6, 2015. The contents of the above-referenced Applications are hereby incorporated by reference in their entirety.

BACKGROUND

Variations of nodule invasiveness and morphology relate to prognosis and patient outcomes. One approach for diagnosing disease is histopathological examination of biopsy tissue. The examination may produce a diagnostic profile based on attributes including cell morphology, cytoplasmic changes, cell density, or cell distribution. Visual characterization of tumor morphology is, however, time consuming, and expensive. Visual characterization is also subjective and thus suffers from inter-rater and intra-rater variability. Conventional visual characterization of nodule morphology by a human pathologist or radiologist may therefore be less than optimal in clinical situations where timely and accurate classification can affect patient outcomes.

Computed tomography (CT) is frequently used to image nodules or other regions of interest. For example, chest CT imagery may be used to detect and diagnose non-small cell lung cancer. However, conventional approaches to analyzing chest CT imagery have been challenged when attempting to distinguish a benign granuloma (Gr) from malignant adenocarcinoma (AC). For example, conventional CT-based approaches may find it difficult, if even possible at all, to reliably discriminate nodules caused by benign fungal infections from non-small cell lung cancer nodules. Histoplasmosis is a common endemic fungal infection in the United States. Granulomas secondary to histoplasmosis infection may appear identical to malignant lung nodules in CT imagery.

Since radiologists may be challenged to reliably distinguish Gr secondary to benign fungal infections from AC in situ using conventional CT approaches in clinically optimal or relevant time frames, invasive procedures may be performed that ultimately result in a negative diagnosis. For example, many patients with benign granulomas are subjected to unnecessary surgical resections and biopsies. These invasive procedures take time, cost money, and put a patient at additional risk. As the number of routine chest CT scans increases with the wide-spread adoption of CT-based lung cancer screening protocols, it would be beneficial to reduce unnecessary thoracotomies, bronchoscopies, biopsies, and other invasive procedures.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
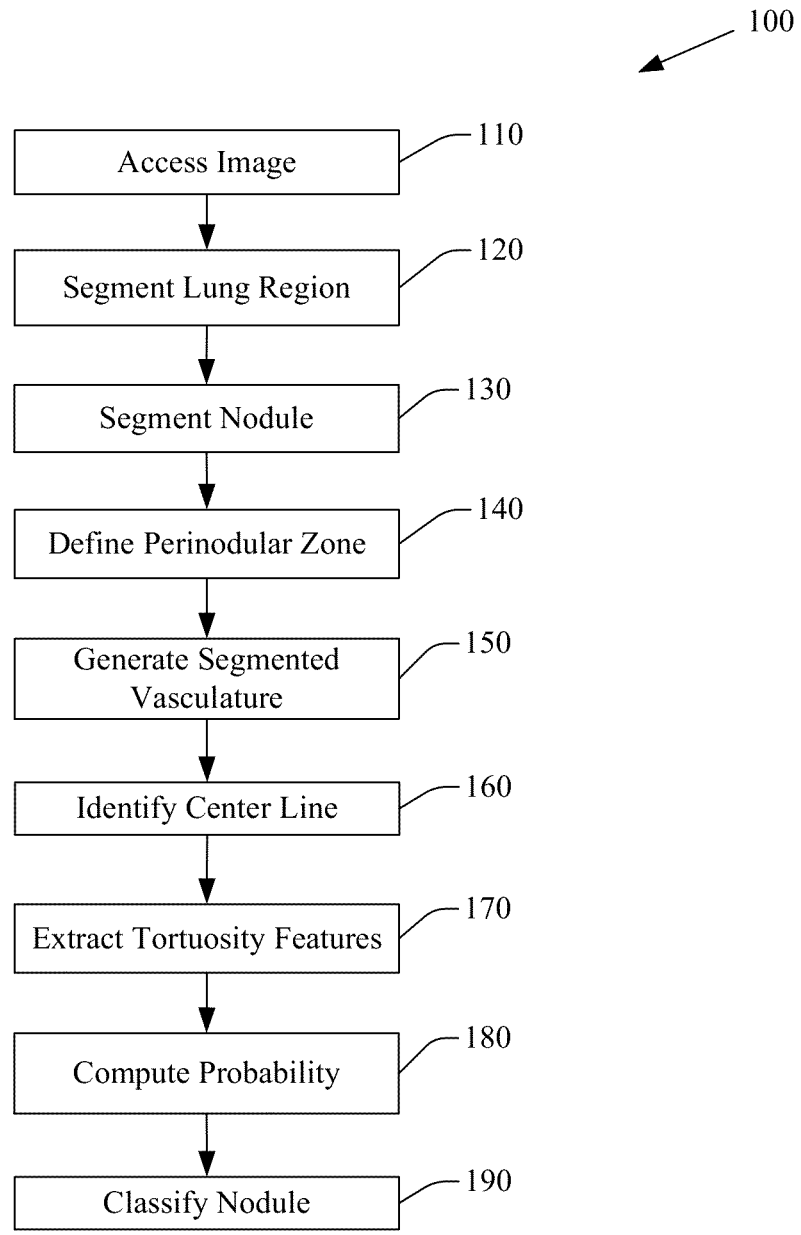
FIG. 1 illustrates an example method of classifying a nodule in a region of tissue.

Variations in tumor invasiveness or morphology may be related to patient prognosis and outcome. Conventional methods of diagnosing disease, including types of cancer, include visual histopathological examination of a biopsy to create a diagnostic profile based on variations in tumor or nodule morphology or invasiveness. However, invasive biopsies and surgical procedures may not always be a convenient or appropriate method for assessing nodules, tumors, or other tissue detected in a radiological image. Invasive biopsies and surgical resections cost money, take time, and put a patient at additional risk. A non-invasive approach that provided improved accuracy compared to conventional CT-based approaches would reduce the number of unnecessary interventions, reduce the dependency on repetitive or higher radiation radiological exams, offer a non-invasive means of assessing response to targeted therapies, and improve patient outcomes. Thus, a timely, non-invasive procedure that results in more accurate discrimination between benign tissue and malignant tissue, or that more accurately predicts a response to treatment, would offer reduced risk to patients while providing economic benefits to the health care system.

CT imagery is conventionally used to differentiate malignant nodules from other, non-cancerous or non-pathological nodules. A nodule may include a ground glass opacity (GGO) nodule or a solitary pulmonary nodule. However, it is difficult to distinguish lung AC nodules from benign Gr nodules, including nodules secondary to histoplasmosis infection, since both AC nodules and Gr nodules can have similar appearances and both can show increased activity on positron emission tomography (PET) or CT evaluation. For example, on chest a CT image, Gr nodules and AC nodules may both demonstrate a spiculated appearance. However, the vascular invasion and lymphangiogenesis in the perinodular habitat of AC is different from that of Gr. In particular, the perinodular zone or habitat of a malignant nodule may exhibit different molecular, radiological, or cellular alterations than the perinodular zone of a benign nodule. Additionally, neoplastic infiltration of malignant nodules may distort neighboring tissue in the perinodular zone. Malignant AC may also demonstrate different histologic patterns than benign Gr, including different lepidic, acinar, papillary, micropapillary, or solid histologic patterns. Furthermore, the tortuosity of vessels in a tumor or nodule's neighborhood may differ between benign and malignant nodules.

Conventional methods of visually assessing nodule invasiveness based on CT imagery are subjective and yield intra and inter-reviewer variability. In one study, for example, more than 30% of suspicious nodules that underwent biopsy for histologic confirmation were determined to be benign Gr caused by prior histoplasmosis infection. Over 1 million people in the United States are subjected to CT guided or bronchoscopic biopsies each year to diagnose nodules detected on CT images, and 60,000 patients a year in the United States are subjected to surgical wedge resections only to find that the suspect nodule is benign. As a result of these invasive procedures, $600,000,000 or more is spent on unnecessary and invasive surgical procedures in the United States.

Conventional CT approaches may focus exclusively on detection of lung nodules, or exclusively on diagnosing malignancy via CT scans. Example apparatus and methods discriminate benign Gr from malignant nodules by analyzing tortuosity features extracted from a perinodular region associated with a nodule. The tortuosity features may be associated with the vasculature detected in the perinodular region or zone. The vasculature associated with malignancy is abnormally shaped. Malignancy makes regional changes to vessel shape and tortuosity. Tortuosity abnormalities appear during the tumor development process and affect initially healthy vessels which are spread beyond the confines of the tumor or tumor margins. The tortuosity of vessels in a tumor's neighborhood (e.g. perinodular zone) contains prognostic information that facilitates discriminating benign nodules from malignant nodules. The tortuosity of vessels in the perinodular zone is also associated with underlying gene-expression patterns. Thus, the tortuosity of vessels in the neighborhood of a tumor, nodule, or other region of tissue may be used by example methods and apparatus to facilitate supporting decisions made to characterize or diagnose the tumor, region of tissue, or nodule.

The perinodular zone may be defined as the region surrounding the nodule, tumor, or region of tissue, extending a threshold distance from the nodule boundary. The perinodular zone may extend, in one embodiment, up to one centimeter from the nodule boundary. In other embodiments, the perinodular zone may extend a different distance from the nodule boundary. Example methods and apparatus distinguish benign granulomas secondary to histoplasmosis fungal infection from malignant carcinomas, and provide decision support in the diagnosis and treatment of patients exhibiting lung nodules in radiological imagery. Distinguishing benign fungal infection from malignant carcinoma facilitates reducing the number of surgical interventions performed that ultimately result in a diagnosis of histoplasmosis or other non-cancerous pathology.

Example methods and apparatus more accurately distinguish malignant lung nodules from benign lung nodules by extracting and analyzing a set of tortuosity features from a perinodular region associated with a lung nodule represented in a radiological image. Example methods and apparatus also facilitate more accurately distinguishing benign tissue from other malignant, cancerous or non-cancerous tissue. For example, methods and apparatus described herein may be used to distinguish breast cancer, brain cancer, rectal cancer, or other cancerous tissues from benign tissue. The set of tortuosity features captures vascular curvature and tortuosity characteristics of vessels associated with the nodule. Tortuosity features, compared to other features employed by conventional approaches, are intensity invariant, and do not exhibit sensitivity to imaging parameters such as scale or resolution that makes conventional approaches sub-optimal. Example methods and apparatus may also extract and analyze a set of features from the nodule to further distinguish benign lung nodules from malignant lung nodules. For example, example methods and apparatus may compute a probability that a nodule is a benign nodule based, at least in part, on the set of features extracted from the perinodular region, and the set of features extracted from the nodule. Since a more accurate distinction is made, example apparatus and methods thus predict patient outcomes in a more consistent and reproducible manner.

Example methods and apparatus predict patient outcomes more accurately than conventional methods by employing computerized tortuosity, textural and morphologic analysis of lung CT imagery to distinguish benign Gr from malignant tumors. Example methods and apparatus may segment a nodule, tumor, or region of tissue from an image background. A spectral embedding gradient vector flow active contour (SEGvAC) model may be employed to segment the nodule from the image background. A perinodular region may be defined with respect to the nodule segmented from the image background. The perinodular region may extend a threshold distance from the nodule. Tortuosity features may be extracted from the perinodular region. Example methods and apparatus also detect and quantify differences in lymphatic vessel density within the perinodular region. Features extracted from the perinodular region or the nodule may facilitate improved detection and analysis of histologic patterns demonstrated by AC, including lepidic patterns, acinar patterns, papillary patterns, micropapillary patterns, or solid patterns. Features extracted from the perinodular region or the nodule may facilitate capturing growth patterns of AC or other malignancies, including angiogenesis, tumor growth, invasion, or metastasis that constitute a neoplastic microenvironment around the nodule. A subset of extracted features may be selected using principal component analysis (PCA)-variable importance projection (VIP). The subset of extracted features may include features that are more discriminative than other, non-selected features. A classification of the nodule image may be generated using quadratic discriminant analysis (QDA) or linear discriminant analysis (LDA).

Example methods and apparatus may train and test a classifier. For example, one embodiment may employ 3-fold cross validation to train a classifier and to test the classifier. The classifier may be a support vector machine (SVM) classifier. For example, a human radiologist may manually delineate and classify one hundred nodules for a training set and thirty nodules for a testing set. Example methods and apparatus may classify the nodule image as a carcinoma, adenocarcinoma, granuloma, or other type of tissue. Other classifications may be employed. Other sizes of training sets or sizes of testing sets may be employed. Example methods and apparatus may also classify the nodule as having a threshold probability of responding to treatment.

Example methods and apparatus may employ an SVM classifier in conjunction with PCA-VIP determined features to discriminate pathologies of interest (e.g. adenocarcinoma, granuloma). The classifier may be trained solely on the training set. A radial-based kernel function (RBF) may be applied to the training set. Members of the training set are defined in instance-label form $(x_i, y_i)$ where $x_i \in R^n$ and $y_i \in \{-1,1\}$. The RBF function is formally defined as:

$$K(x_i, x_j) = \exp(\gamma \|x_i - x_j\|^2), \gamma > 0.$$

Example methods and apparatus thus improve on conventional methods by more accurately distinguishing between pathological and benign lung nodules. Example methods and apparatus distinguish granuloma from carcinoma with an accuracy of at least 0.86 area under the curve (AUC).

By increasing the accuracy with which malignant nodules are distinguished from benign nodules, or by which response to treatment is predicted, example methods and apparatus produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately characterize nodules. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates an example computerized method 100 for characterizing a nodule in a region of tissue. Method 100 includes, at 110, accessing an image of a region of tissue. Accessing the image may include accessing a no-contrast CT image of a region of lung tissue demonstrating cancerous pathology. Accessing the image may include retrieving electronic data from a computer memory, receiving a computer file over a computer network, or other computer or electronic based action. In one embodiment, the image is a 1 mm to 5 mm thick, no-contrast chest CT image. In one embodiment, the number of slices per scan may range from 126 to 385, and a slice may have an XY planar resolution of 512 pixels by 512 pixels, with a 16 bit gray scale resolution indicated in Hounsfield Units (HU). In another embodiment, other image types, modalities, resolutions, scales, slices per scan, or image dimensions may be used.

Method 100 also includes, at 120, segmenting a lung region in the image. In one embodiment, segmenting the lung region from surrounding anatomy includes distinguishing the lung region from the surrounding anatomy using a multi-threshold based approach. In other embodiments, the lung region may be segmented from the surrounding anatomy using other, different approaches. In still other embodiments, other types or regions of tissue (e.g. breast, brain, prostate, rectal) may be segmented from surrounding anatomy.

Method 100 also includes, at 130, segmenting a nodule in the image. Segmenting the nodule includes defining a nodule boundary. The nodule boundary may be extracted from the image. The nodule may be automatically segmented by distinguishing nodule tissue within the image from the background of the image. In one embodiment, the nodule tissue may be automatically distinguished using a heuristic threshold based approach. In another embodiment, the nodule tissue may be automatically distinguished using SEGvAC segmentation. In another embodiment, other segmentation approaches may be employed, including threshold based segmentation, deformable boundary models, active-appearance models, active shape models, graph based models including Markov random fields (MRF), min-max cut approaches, or other image segmentation approaches. In another embodiment, the nodule may be manually segmented.

In one embodiment, SEGvAC segmentation includes separating the lung region from the surrounding anatomy in the image. A non-linear embedding representation of the lung may be employed to separate the image of the lung from the surrounding thoracic anatomy. The SEGvAC approach also includes removing non-nodule structures from the image using a rule-based classifier. The SEGvAC approach further includes extracting the nodule surface from the image using active contour based segmentation. Example methods and apparatus employing a SEGvAC approach improve on conventional approaches by eliminating segmentation errors caused by both pleura and vessel attached nodules by separating lung tissues and removing non-nodule structures.

SEGvAC segmentation employs a spectral embedding based active contour. Spectral embedding (SE) is a non-linear dimensional reduction method that forms an affinity matrix via a pre-specified kernel function. The kernel function facilitates a mapping of an original set of image features or intensities to a new kernel space where spectral decomposition may be applied to the corresponding graph Laplacian. An individual pixel from the original lung CT image is then represented by the corresponding value of the eigenvectors obtained by spectral decomposition. SE representation of the lung provides strong gradients at the margin of the nodules which facilitate an active contour model to stop evolving at the nodule boundary. The SEGvAC approach employed by example methods and apparatus further includes a gradient vector flow field (GVF) active contour. The GVF forces are calculated for the image domain. The GVF forces drive the active contour.

In one embodiment, the SEGvAC segmentation approach includes isolating lung regions from surrounding anatomy illustrated in the CT image to generate an initial lung mask. Example methods and apparatus identify an optimal threshold to separate body voxels from non-body voxels. A non-body voxel is a low density voxel representing lung and surrounding air. The initial lung mask is further refined by applying morphological hole filling to the logical complement of the initial lung mask.

Upon extraction of the initial region of interest (e.g. lung region) from the CT image, example methods and apparatus may perform an automatic segmentation of the nodule. Example methods and apparatus employ an active contour scheme to segment the nodule. In one embodiment, the image plane $\Omega=R^2$ is partitioned into two regions by a curve $\gamma$. The foreground region of the image plane is defined as $\Omega_1$ and the background region of the image plane is defined as $\Omega_2$. Thus, the image plane is comprised of the union of regions of interest, background, and evolving contour ($\Omega=\Omega_1 \cup \Omega_2 \cup \gamma$).

In simplified form, the energy functional of an edge-based active contour is defined as $$E=\alpha E_1+\beta E_2 \quad (eq.\ 1)$$

where $E_2$ refers to internal forces used to keep the integrity and elasticity of the contour and where $E_1$ is the image force.

The image force $E_1$ is defined as $$E_1=\int_\gamma g(v(c))dc \quad (eq.\ 2)$$

where c=(x,y) corresponds to a voxel in the two dimensional (2D) image plane, v(c) is the intensity value of the voxel c, and g(v(c)) is defined as $$g(v(c)) = \frac{1}{1+\psi(v(c))}. \quad (eq.\ 3)$$

The gradient function $\psi(v(c))$ is conventionally calculated by a gray level gradient. Example methods and apparatus employ a tensor gradient function derived from the spectral embedding representation. By using the tensor gradient function, example methods and apparatus facilitate the generation of improved region and boundary-based statistics, and stronger gradients, compared to conventional approaches.

Example methods and apparatus employ a GVF active contour. The GVF forces calculated for the image domain are used to drive the active contour. Active contours driven by GVF forces do not need to be initialized very closely to the boundary. The GVF forces are calculated by applying generalized diffusion equations to both components of the gradient of an image edge map, where the image edge map is of the original CT image. In one embodiment, the SEGvAC approach is initialized using a single point and click on a region of interest (e.g. nodule, tumor). In another embodiment, the SEGvAC approach may be initialized automatically.

In one embodiment, before employing the SEGvAC approach, example methods and apparatus may employ a rule-based classifier to remove unwanted structures from the image based on geometric properties of the unwanted structures. The geometric properties of the unwanted structures may be 3D geometric properties. The 3D geometric properties may include bounding box measures and elongation of 3D structures defined as the length of the major axis of the nodule divided by the length of the minor axis of the nodule. Lung nodules are frequently 5 mm to 30 mm long. Thus, 3D structures that do not fit this size may be eliminated using the rule-based classifier. Candidate objects for inclusion or exclusion may be examined in terms of convexity or elongation measures for distinguishing vessel-like structures from more convex or sphere-like objects. In one embodiment, a set of morphological operations, including erosion and closing operations, may be employed to filter objects associated with vessel-connected nodules. Removing unwanted structures improves the performance of systems and devices employing example methods and apparatus by reducing the computational complexity required to accurately characterize a tumor, nodule, or other region of tissue, compared to conventional approaches.

Method 100 also includes, at 140, defining a perinodular zone associated with the nodule. In one embodiment, defining the perinodular zone includes generating an outer perinodular boundary by dilating the nodule boundary a threshold amount. In one embodiment, the threshold amount is from 5 mm to 7 mm. In another embodiment, another, different threshold amount may be used. For example, the threshold amount may be from 3.5 mm to 5 mm. The threshold amount may be based on a unit of distance (e.g. mm, cm) or may be based on a pixel size, an image resolution, a number of pixels, or other unit of measurement. For example, in one embodiment in which the CT image has a pixel size of 0.7 mm center to center, the threshold amount may be defined as 7 pixels. Thus, in this example, a mask of the nodule defined by the nodule boundary may be dilated by seven pixels. Defining the perinodular region further includes subtracting the nodule from the region defined by the outer perinodular boundary. Thus, for example, in one embodiment, the perinodular region may be bounded by the outer perinodular boundary and the nodule boundary. In one embodiment, the threshold amount is user adjustable.

Figure 3:
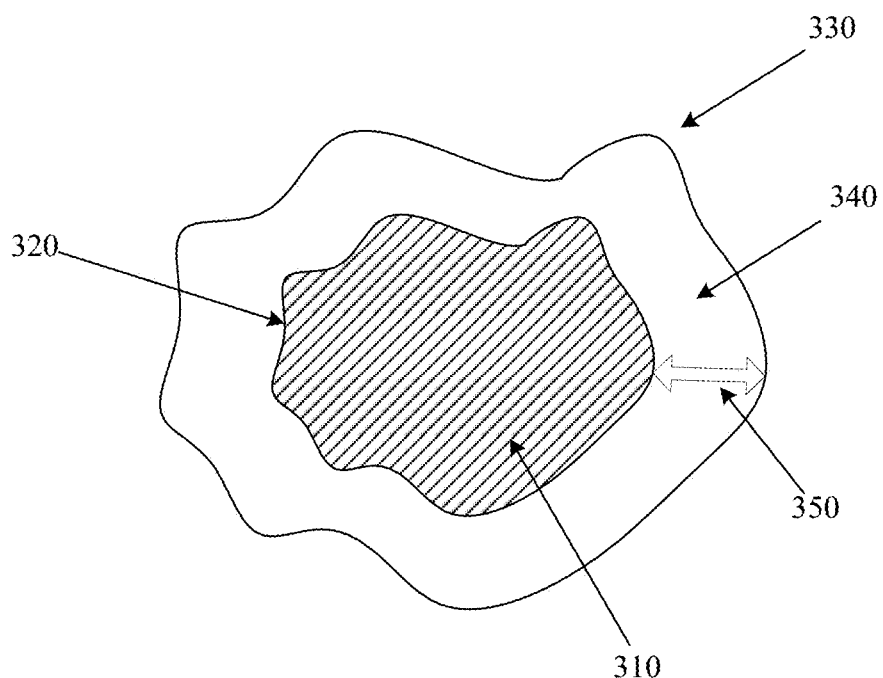
FIG. 3 illustrates a perinodular zone associated with a nodule.

FIG. 3 illustrates an example perinodular region 340 associated with a nodule 310. Perinodular region 340 is bounded by outer perinodular boundary 330 and nodular boundary 320. In one embodiment, example methods and apparatus dilate nodule boundary 310 by an amount 350, resulting in the outer perinodular boundary 330. Amount 350 may be, for example, one centimeter, 10 pixels, or another, different amount.

In another embodiment, the perinodular boundary may be generating using other techniques. For example, the perinodular boundary may be defined as a function of a property of the nodule. The property of the nodule may include, for example, a diameter, a radius, a perimeter, an area, a volume, or other property of the nodule. The function may define the perinodular region as, for example, a dilation of the nodule boundary, where the dilation ratio is defined by a magnitude of an axis of the nodule. In another embodiment, the perinodular boundary may be defined as a disc of a threshold radius defined about the centroid of the nodule, or defined on the focal points of an elliptical representation of the nodule. In one embodiment, the perinodular boundary may be manually defined. Other approaches or combinations of approaches may be used to define the perinodular boundary.

In one embodiment, method 100, at 140, further includes removing pixels having less than a threshold level of HU from the perinodular zone. Lung parenchyma have HU values of approximately −500. In one embodiment, the threshold level is −900 HU. Removing pixels having less than a threshold level of HU from the perinodular zone facilitates radiomic analysis of the perinodular zone by removing confounding information from the image being analyzed, or by reducing the amount of computational resources required to extract features from the perinodular zone compared to conventional approaches. For example, pixels representing air, which has an HU value of approximately −1000, may be removed from the image. Other tissue, including bone, may also be removed. For example, pixels representing cancellous bone (+700 HU) or cortical bone (+3000 HU) may be removed.

Figure 5:
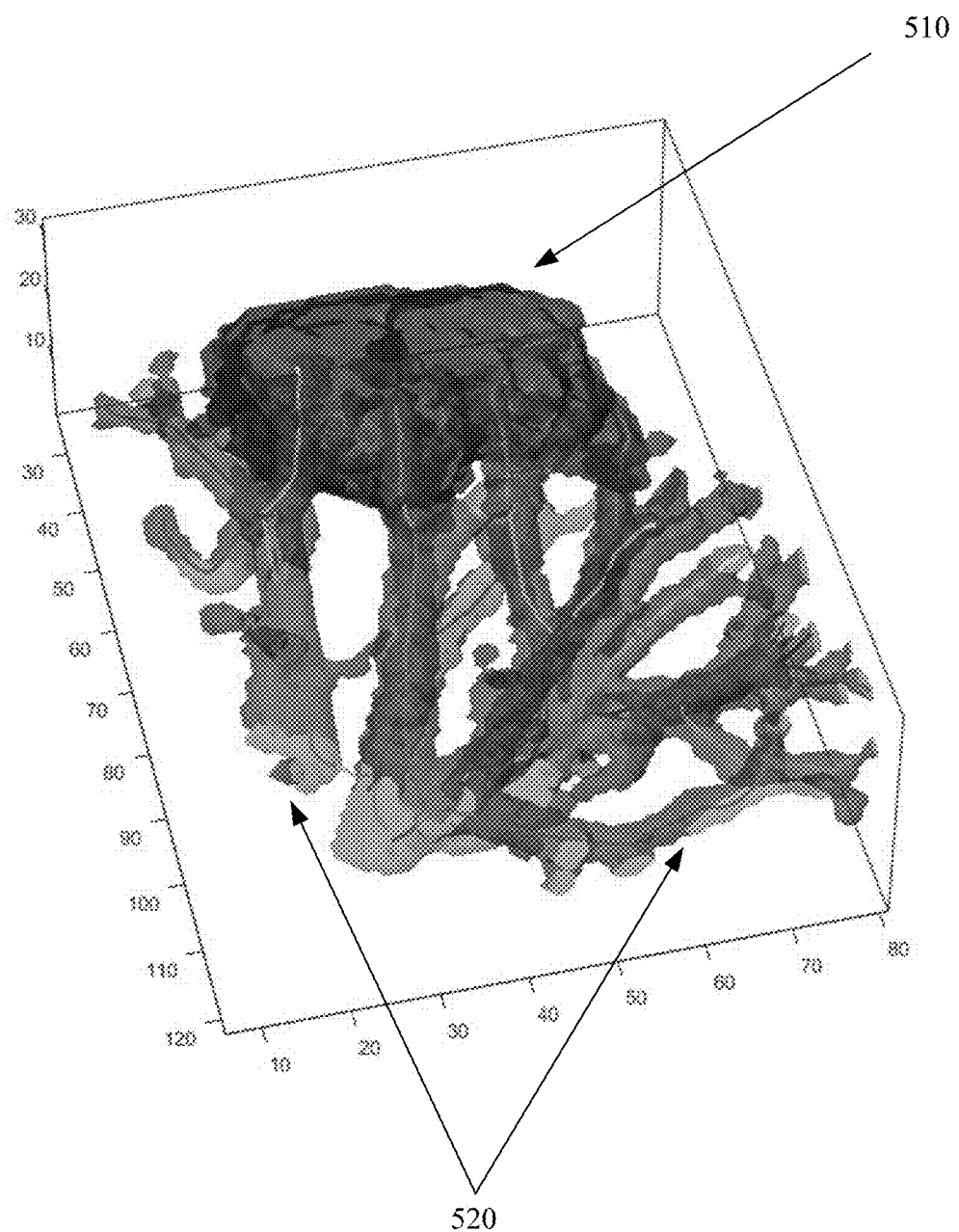
FIG. 5 illustrates an example 3D segmented vasculature.

Method 100 also includes, at 150 generating a segmented vasculature. The segmented vasculature may be a three-dimensional (3D) segmented vasculature segmented from the perinodular zone. In one embodiment, example methods and apparatus may automatically segment vessels associated with the nodule. FIG. 5 represents a 3D segmented vasculature 520 associated with a nodule 510.

Figure 6:
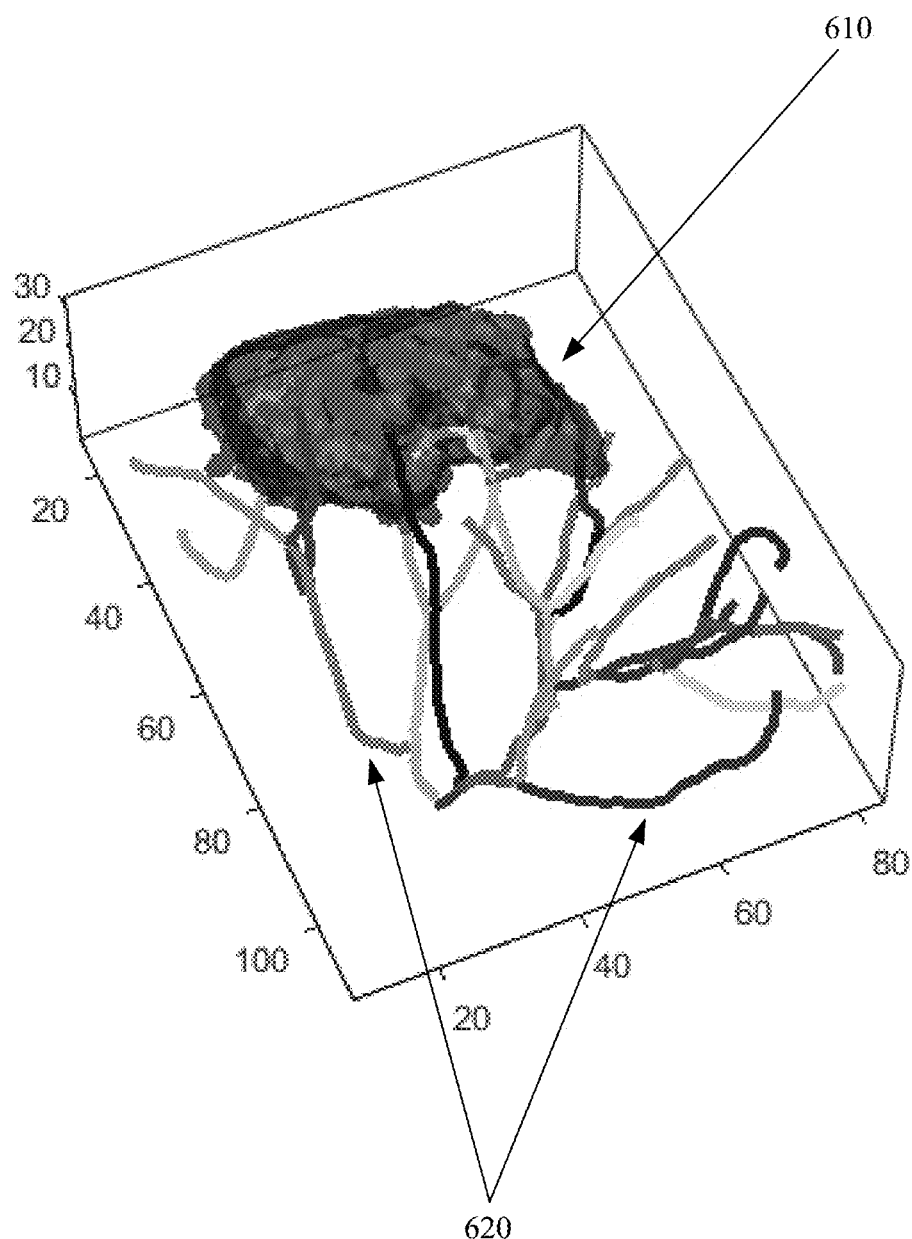
FIG. 6 illustrates an example of centerlines of an example 3D segmented vasculature.

Method 100 also includes, at 160, identifying a centerline of the 3D segmented vasculature. For example, method 100 may, at step 160, identify a centerline of a vessel and branching points associated with the vessel. In one embodiment, method 100 may identify the centerline or branching points using a fast marching approach. In another embodiment, the centerline or branching points may be identified using a different approach. FIG. 6 represents detected centerlines 620 associated with a nodule 610 that is similar to nodule 510.

Method 100 also includes, at 170, extracting a set of tortuosity features from the image. The set of tortuosity features may be a set of perinodular tortuosity features based, at least in part, on the centerline. In one embodiment, method 100 calculates the torsion for a vessel segment using a distance metric. The torsion of a vessel segment is defined as 1-(Distance/Length) where distance is the Euclidean distance of the start and end point of the segment, and where length is the number of voxels along the vessel segment. Method 100, at 170, also extracts the curvature of a vessel segment. Curvature at a voxel of a vessel segment is proportional to the inverse of an osculating circle's radius. The osculating circle is fitted to a collection of three neighboring points along the centerline of a vessel. For a plurality of points along the center line of a vessel, method 100 fits a circle to compute the curvature of a specific point. Method 100 then computes mean and standard deviation of the curvature for points along the vessel. Method 100 may also capture branching statistics associated with the vessel.

The tortuosity features describe vessels associated with the nodule. Example methods and apparatus use the tortuosity features to quantify a measure of aggressiveness or irregularity in vessels associated with a nodule, tumor, or region of tissue. The set of tortuosity features includes the mean of torsion of a vessel segment, or the standard deviation of torsion of a vessel segment. The set of tortuosity features also includes the mean and standard deviation of the mean curvature of a group of vessel segments. The set of tortuosity features also includes the mean and standard deviation of a vessel segment curvature and a total vessel segment length. The set of tortuosity features may also include branching statistics associated with the vessel. In one embodiment, the set of tortuosity features includes at least seven tortuosity features. In another embodiment, the set of tortuosity features may include other numbers of tortuosity features, or other, different tortuosity features. In one embodiment, method 100 may also select a subset of tortuosity features from the set of tortuosity features. The subset of tortuosity features may include a torsion standard deviation, a standard deviation of a curvature, and a number of branches.

Method 100 also includes, at 180, computing a probability that the nodule is benign. The probability may be based, at least in part, on the set of perinodular tortuosity features. In one embodiment, computing the probability that the nodule is benign includes computing the probability that the nodule is a benign Gr secondary to histoplasmosis infection. In another embodiment, computing the probability that the nodule is benign includes computing the probability that the nodule is another type of benign nodule. Example methods and apparatus may also compute a probability that the nodule is malignant. For example, methods and apparatus described herein may compute the probability that the nodule or tumor is a breast cancer nodule, a brain cancer tumor, or other, different type of nodule or tumor. Example methods and apparatus may also compute a probability that the nodule will respond to treatment. Example methods and apparatus may also compute a probability that a different type of cancerous pathology identified in the image will respond to a different treatment.

Method 100 also includes, at 190, classifying the nodule. Classifying the nodule may include controlling a computer aided diagnosis (CADx) system to generate a classification of the nodule represented in the image. The classification may be based, at least in part, on the set of perinodular texture features or the probability. In one embodiment, the CADx system generates the classification of the image of the nodule using a QDA classifier. In another embodiment, the CADx system may generate the classification using other, different types of classifier. The classifier may be an SVM classifier trained and tested on a set of images of pre-classified nodules. The set of images of pre-classified nodules may include an image of a region of tissue demonstrating adenocarcinoma pathology annotated by an expert radiologist. In another embodiment, the set of images of pre-classified nodules may include an image of a region of tissue demonstrating other, different pathologies, including breast cancer. In one embodiment, controlling the CADx system to generate the classification of the nodule based, at least in part, on the set or perinodular texture features or the probability, includes classifying the image of the nodule as malignant adenocarcinoma or benign Gr secondary to histoplasmosis infection. In another embodiment, example methods and apparatus control the CADx system to generate a classification of the nodule based, at least in part, on the set of perinodular texture features, or on the probability that the nodule will respond to treatment. The SVM classifier classifies the nodule with an accuracy of at least 0.86 area under the curve (AUC).

Example methods and apparatus facilitate more accurate characterization of nodules found in CT images than conventional approaches. Example methods and apparatus thus improve on conventional methods by characterizing nodules as benign Gr secondary to histoplasmosis infection, as carcinomas, or as adenocarcinomas with greater accuracy and with less subjective variability than conventional methods. Example methods and apparatus therefore facilitate more judicious application of biopsies and surgical resection in a population undergoing CT screening for lung cancer.

Using a more appropriately determined and applied treatment may lead to less therapeutics being required for a patient or may lead to avoiding or delaying a biopsy, a resection, or other invasive procedure. When regions of cancerous tissue, including nodules detected in CT scans, are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes.

While FIG. 1 illustrates various actions occurring in serial, it is to be appreciated that various actions illustrated in FIG. 1 could occur substantially in parallel. By way of illustration, a first process could delineate a nodule in a CT image, a second process could define a perinodular zone in the CT image, and a third process could extract perinodular tortuosity features from the CT image. While three processes are described, it is to be appreciated that a greater or lesser number of processes could be employed and that lightweight processes, regular processes, threads, and other approaches could be employed.

Figure 2:
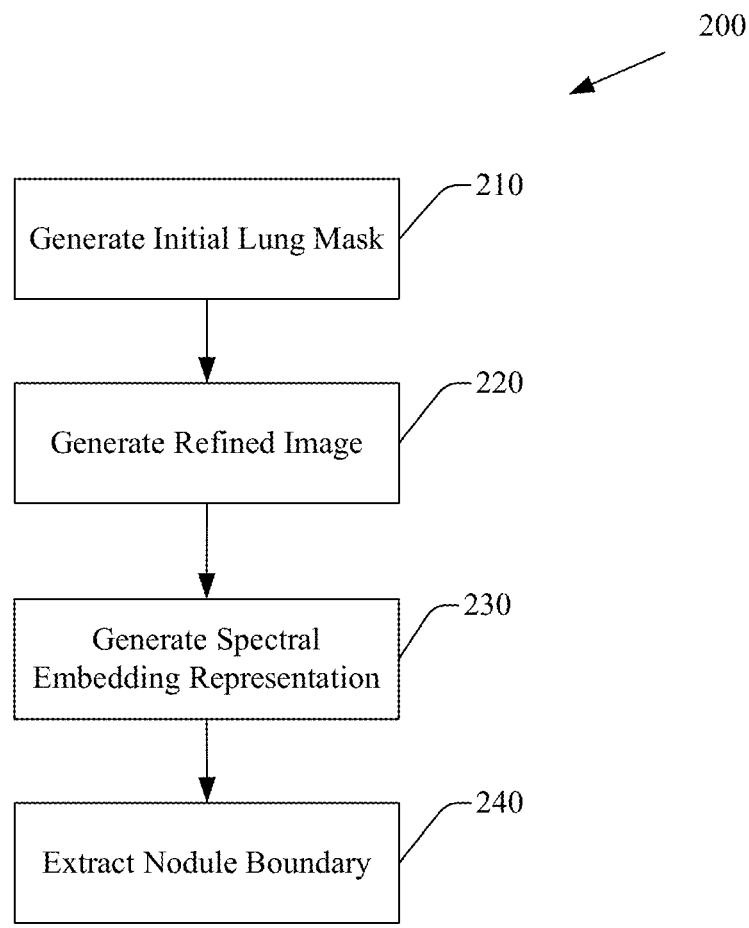
FIG. 2 illustrates an example method for segmenting a nodule.

FIG. 2 illustrates an example method 200 for distinguishing nodule tissue in a CT image from a background of the image using a SEGvAC approach. Method 200 is suitable for use by example methods and apparatus described herein, including method 100, method 700, method 1000, or apparatus 800. Method 200 includes, at 210 generating an initial lung mask. In one embodiment, generating the initial lung mask includes separating a lung region represented in the image from surrounding lung anatomy. In one embodiment, generating the initial lung mask includes refining the initial lung mask by applying morphological hole-filling to a logical complement of the initial lung mask.

Method 200 also includes, at 220, generating a refined image. Generating the refined image includes removing a non-granuloma structure from the initial lung mask using a rule-based classifier. In one embodiment, the rule-based classifier selects a non-granuloma structure to remove from the initial lung mask based on a convexity measure of the non-granuloma structure, or an elongation measure of the non-granuloma structure. The rule-based classifier may select a non-granuloma structure to remove based on 3D geometric properties of structures in the perinodular zone. The 3D properties may include bounding box measures and elongation of the 3D structure defined as the length of the major axis divided by the length of the minor axis. In one embodiment, 3D structures that do not fit within a size criteria range of 5 mm to 30 mm are removed by the rule-based classifier. In another embodiment, morphological operations, including erosion operations or closing operations, are used to isolate vessel-connected nodules.

Method 200 also includes, at 230, generating a spectral embedding (SE) representation by projecting at least one refined image into a 3D SE space. In one embodiment, generating an SE representation includes forming an affinity matrix via a pre-specified kernel function. The kernel function facilitates mapping a set of image features to a new kernel space, where spectral decomposition is applied to a corresponding graph Laplacian. A pixel in the CT image is then represented by a corresponding value of an eigenvector obtained via the spectral decomposition step.

Method 200 also includes, at 240, extracting a nodule boundary from the SE representation. Extracting the nodule boundary may include calculating a tensor gradient function derived from the SE representation. In one embodiment, extracting the nodule boundary from the SE representation includes extracting the nodule boundary using a gradient vector flow field (GVF) active contour model. A GVF force drives the active contour. In one embodiment, the GVF force is calculated based on a generalized diffusion equation applied to a component of an image edge map of the CT image of the region of lung tissue.

Figure 4:
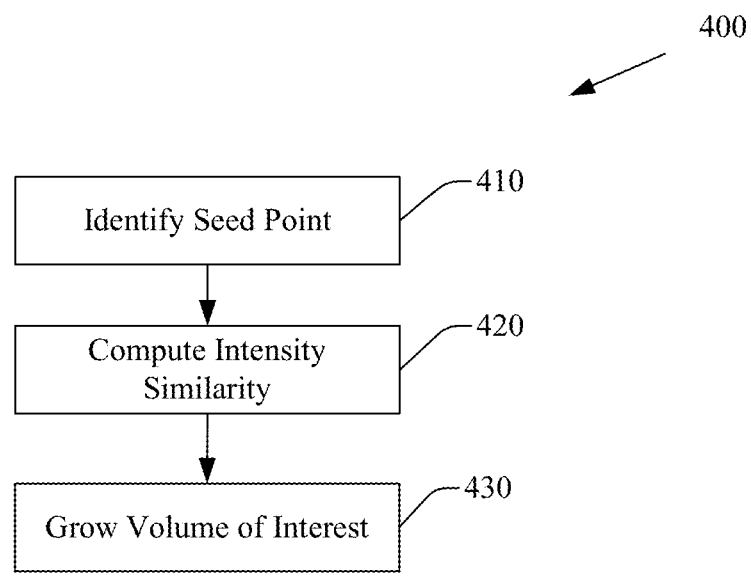
FIG. 4 illustrates an example method for generating a three-dimensional (3D) segmented vasculature.

FIG. 4 illustrates a method 400 for segmenting a vessel from the perinodular zone. Method 400 is suitable for implementation with method 100, method 700, method 1000, apparatus 800, or other methods and apparatus described herein. Method 400 includes, at 410, identifying a seed point within a volume of interest. A seed point may be a member of a plurality of seed points. A seed point has an intensity. The volume of interest is within the perinodular zone. In one embodiment, the volume of interest is outside the perinodular zone.

Method 400 also includes, at 420, computing an intensity similarity. The intensity similarity may represent the similarity between an intensity of a first member of the plurality of seed points, and an intensity of a second, different member of the plurality of seed points. The intensity similarity may represent the similarity of intensity between other, different numbers of seed points.

Method 400 also includes, at 430, growing the volume of interest. Example methods and apparatus may grow the volume of interest using a 3D region growing approach. The 3D region growing approach may be based, at least in part, on the intensity similarity.

Methods, apparatus, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Figure 7:
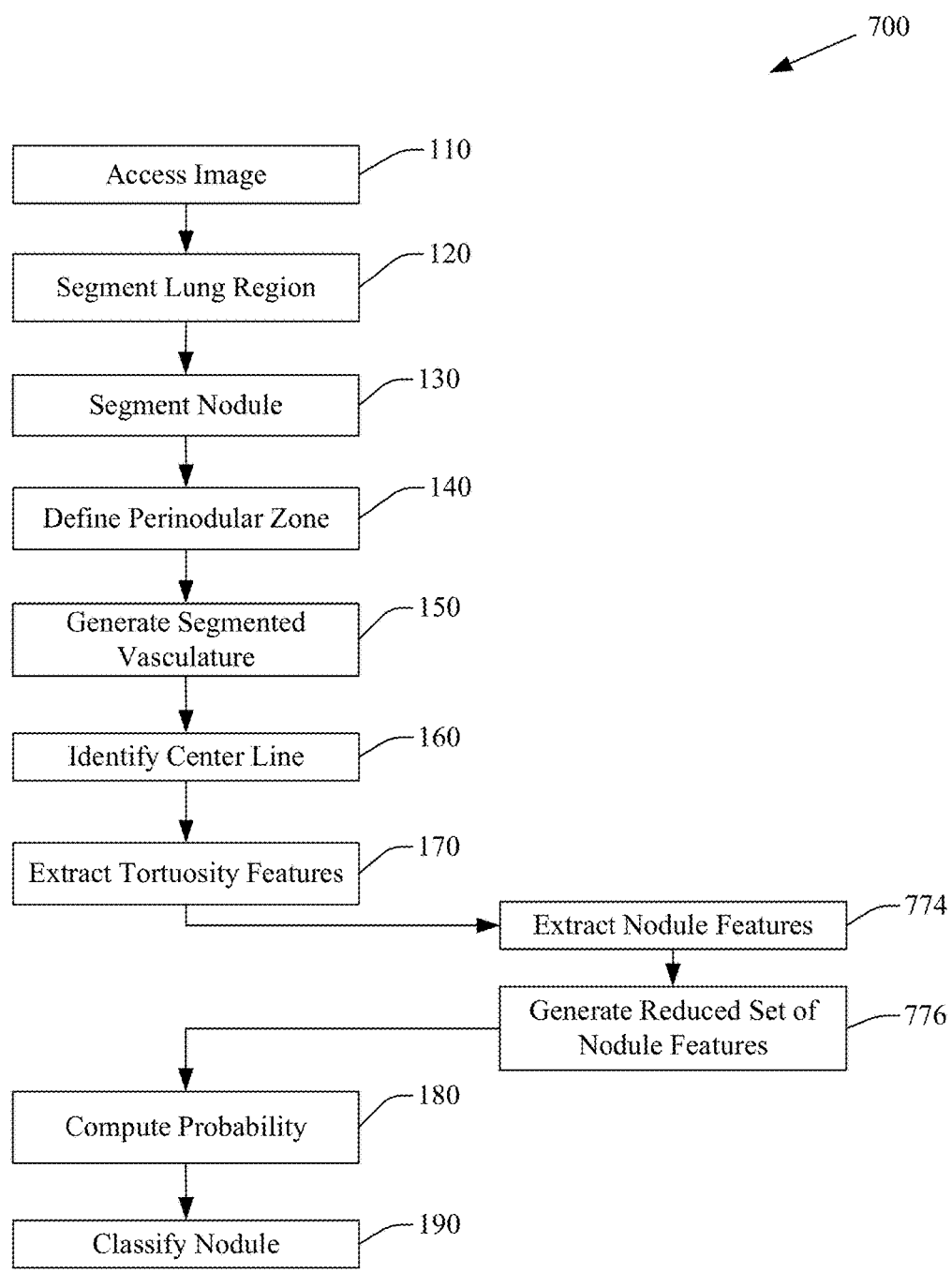
FIG. 7 illustrates an example method for classifying a nodule in a region of tissue.

FIG. 7 illustrates an example method 700 for characterizing a nodule in a region of lung tissue. Method 700 is similar to method 100 but includes additional actions. Method 700 includes actions 110, 120, 130, 140, 150, 160, 170, 180, and 190, which are similar to actions 110, 120, 130, 140, 150, 160, 170, 180, and 190 described above with respect to method 100.

Method 700 also includes, at 774, extracting a set of nodule features from the nodule. The set of nodule features may include a set of shape features or a set of texture features. In one embodiment, extracting the set of nodule features includes extracting a set of shape features from the image of the nodule. The set of shape features includes a location feature, a size feature, a width feature, a height feature, a depth feature, a perimeter feature, an eccentricity feature, an eccentricity standard deviation, a compactness feature, a roughness feature, an elongation feature, a convexity feature, an extend feature, an equivalent diameter feature, or a sphericity feature. The location feature describes the spatial information of a pixel in the image of the nodule, the size feature describes the number of pixels within the segmented image of the nodule, and the perimeter feature describes the distance around the boundary of the segmented nodule. The eccentricity feature describes the eccentricity of an ellipse that has the same second moments as the nodule. The compactness feature describes the iso-perimetric quotient of the nodule. The roughness feature describes the perimeter of a lesion in a slice of the image of the nodule divided by the convex perimeter of the lesion. The elongation feature describes the ratio of minor axis to the major axis of the image of the nodule, and the convexity feature describes the ratio of a tumor image slice to the convex hull of the tumor. The extend feature describes the ratio of pixels in the tumor region to pixels in the total bounding box. The equivalent diameter feature describes the diameter of a circle having the same area as a tumor image slice, and the sphericity feature describes the three-dimensional compactness of the nodule. In one embodiment the set of shape features includes at least twenty-four shape features. In another embodiment, the set of shape features may include other numbers of shape features, or other, different shape features. A feature may be calculated in 3D space, or in two dimensional (2D) space. For example, width, height, depth, or sphericity features may be calculated in 3D space.

In one embodiment, extracting the set of nodule features from the nodule includes extracting a set of texture features. The set of texture features includes a gray-level statistical feature, a steerable Gabor feature, a Haralick feature, a Law feature, a Law-Laplacian feature, a local binary pattern (LBP) feature, inertia, a correlation feature, a difference entropy feature, a contrast inverse moment feature, a co-occurrence of local anisotropic gradient orientations (Co-LIAGe) features, or a contrast variance feature. In one embodiment, the set of texture features includes at least twenty four texture features. In other embodiments, other numbers or types of texture features may be extracted.

Method 700 also includes, at 776, generating a reduced set of nodule features. In one embodiment, generating the reduced set of nodule features includes selecting a subset of shape features from the set of shape features. In one embodiment, the subset of shape features includes eccentricity, eccentricity standard deviation, or elongation features. In another embodiment, the subset of shape features may include other, different shape features. The subset of shape features may be selected from the set of shape features using PCA feature ranking or PCA-VIP feature ranking. In one embodiment, generating the reduced set of nodule features includes selecting a subset of texture features from the set of texture features. The subset of texture features may be selected from the set of texture features using PCA feature ranking or PCA-VIP feature ranking.

Method 700 also includes, at 190, controlling the CADx system to generate a classification of the image of the nodule. In one embodiment, the CADx system classifies the nodule as benign or malignant. In one embodiment, the CADx system classifies the nodule as a benign Gr secondary to histoplasmosis infection, or as a malignant adenocarcinoma. The CADx system may employ an SVM to generate the classification. The classification may be based, at least in part, on the set of tortuosity features, and the set of nodule features. Basing the classification on both the set of tortuosity features and the set of nodule features improves on conventional approaches by increasing the accuracy with which the image may be classified. In one embodiment, the CADx system generates the classification of the image of the nodule using an LDA classifier or a QDA classifier. The LDA classifier or the QDA classifier may be trained or tested on a set of images pre-classified as Gr, adenocarcinoma, or other pathology. In another embodiment, the CADx system may classify the nodule as likely to respond to a treatment.

Figure 10:
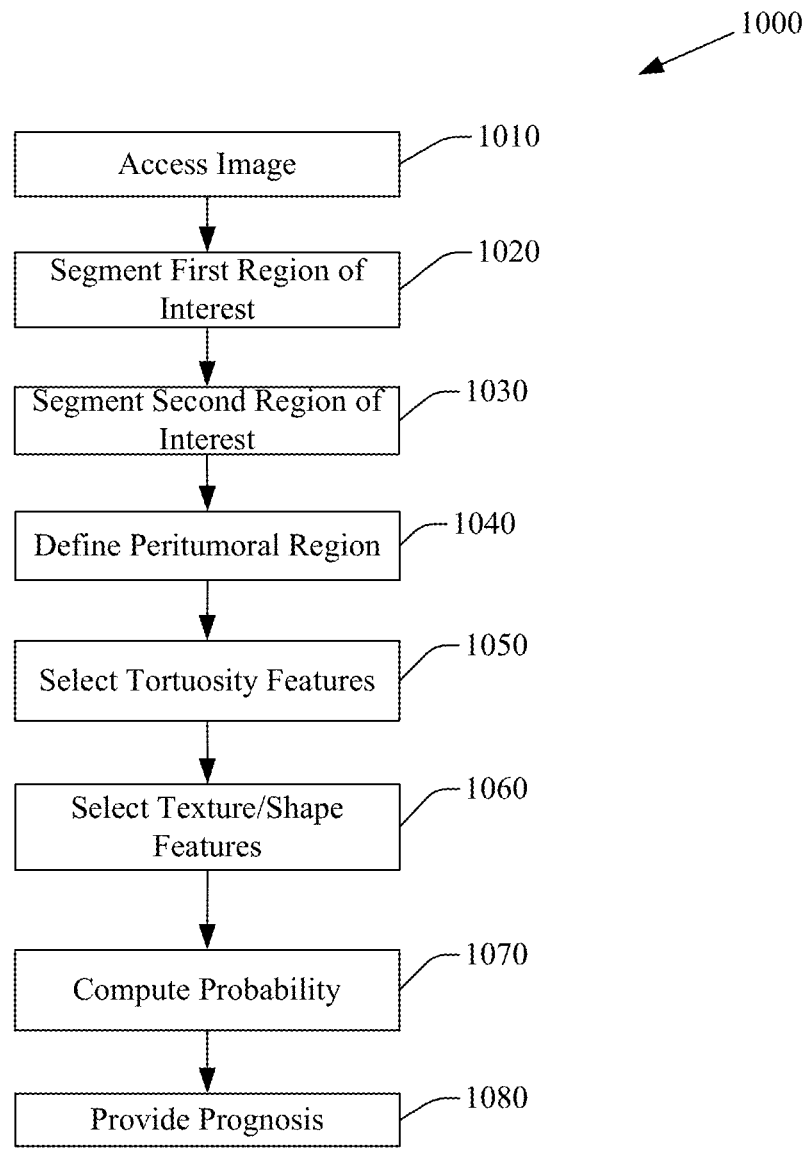
FIG. 10 illustrates an example method for providing a prognosis prediction for a region of interest represented in a medical image.

FIG. 10 illustrates an example method 1000 for distinguishing benign tissue from malignant tissue in a medical image. The medical image may be a chest CT image, or other radiological image. Method 1000 includes, at 1010 accessing an image of a region of tissue demonstrating a pathology, including a cancerous pathology. In one embodiment, the image is a 1 mm to 5 mm thick, no-contrast chest CT image. In another embodiment, other image types or image dimensions may be used. For example, the image may be a dynamic contrast enhanced (DCE) magnetic resonance (MR) image. Accessing the image may include retrieving electronic data from a computer memory, receiving a computer file over a computer network, or other computer or electronic based action.

Method 1000 also includes, at 1020, segmenting first region of interest in the image from the background of the image. Segmenting the first region of interest in the image from the background of the image involves identifying the portion of the image that represents the first region of interest to distinguish that portion from the background. In one embodiment, the first region of interest is automatically segmented from the background of the image. In another embodiment, a human radiologist manually delineates the first region of interest from the background of the image. In another embodiment, vessels associated with the first region of interest are also segmented. The first region of interest may be segmented using a multi-threshold approach, a heuristic threshold approach, or other segmentation approach.

Method 1000 also includes, at 1030 segmenting a second region of interest in the image. The second region of interest may be segmented from the first region of interest. The second region of interest may be a tumor, a nodule, or other region of tissue. Segmenting the second region of interest may include defining a boundary for the second region of interest, for example, a nodule boundary. In one embodiment, the second region of interest may be automatically segmented from the first region of interest using SEGvAC segmentation. In another embodiment, the second region of interest is segmented manually.

Method 1000 also includes, at 1040, defining a peritumoral region. The peritumoral region is defined based, at least in part, on the second region of interest or the boundary for the second region of interest. The peritumoral region may be generated by defining a mask and subtracting the second region of interest from the mask. For example, the mask may be generated by dilating the boundary for the second region of interest by a threshold amount. The second region of interest may be subtracted from the mask to define the peritumoral region.

Method 1000 also includes, at 1050, selecting a set of tortuosity features from the peritumoral region. The set of tortuosity features may include the mean of torsion of a vessel segment, or the standard deviation of torsion of a vessel segment. The set of tortuosity features may also include the mean and standard deviation of the mean curvature of a group of vessel segments. The set of tortuosity features may also include the mean and standard deviation of a vessel segment curvature and a total vessel segment length. In one embodiment, the set of tortuosity features includes at least seven tortuosity features. In another embodiment, the set of tortuosity features may include other numbers of tortuosity features, or other, different tortuosity features.

Method 1000 also includes, at 1060, selecting a set of texture features or a set of shape features from the peritumoral region. In one embodiment, the set of texture features may include a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, a CoLIAGe feature, or a contrast variance feature. In another embodiment, other, different texture features may be selected. Method 1000 also includes, at 1060, selecting a set of shape features from the nodule. The set of shape features may include a location feature, a size feature, a perimeter feature, an eccentricity feature, an eccentricity standard deviation, a compactness feature, a roughness feature, an elongation feature, a convexity feature, an equivalent diameter feature, a radial distance feature, an area feature, or a sphericity feature. In another embodiment, other, different shape features may be selected. The set of tortuosity features, the set of shape features, or the set of texture features may be reduced using PCA-VIP feature ranking or PCA feature ranking.

Method 1000 also includes, at 1070, generating a probability that the second region of interest is benign. Generating the probability may include generating a classification for the second region of interest based, at least in part, on the set of texture features, the set of shape features, or the set of tortuosity features. In one embodiment, the classification is made based on the set of texture features. In another embodiment, the classification is based on the set of shape features. In still another embodiment, the classification is based on the set of texture features, the set of shape features, and the set of tortuosity features. The set of shape features, the set texture features, or the set of tortuosity features may be selected to achieve a threshold level of accuracy when classifying the second region of interest. In one embodiment, method 1000 classifies a tumor or a nodule as a carcinoma or a granuloma. In another embodiment, the second region of interest is classified as frank invasive, minimally invasive, or non-invasive. The classification may be made by a CADx system using an SVM, a QDA classifier, or an LDA classifier.

Method 1000 also includes, at 1080, providing a prognosis prediction based on the probability. For example, method 1000, at 1070, may provide a probability that the second region of interest is benign, and method 1000 at 1080, may provide a prognosis prediction based on the probability. Method 1000 may, alternately, provide a probability that the second region of interest is malignant, or that the second region of interest will respond to a treatment.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, method 400, method 700, and method 1000. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 8:
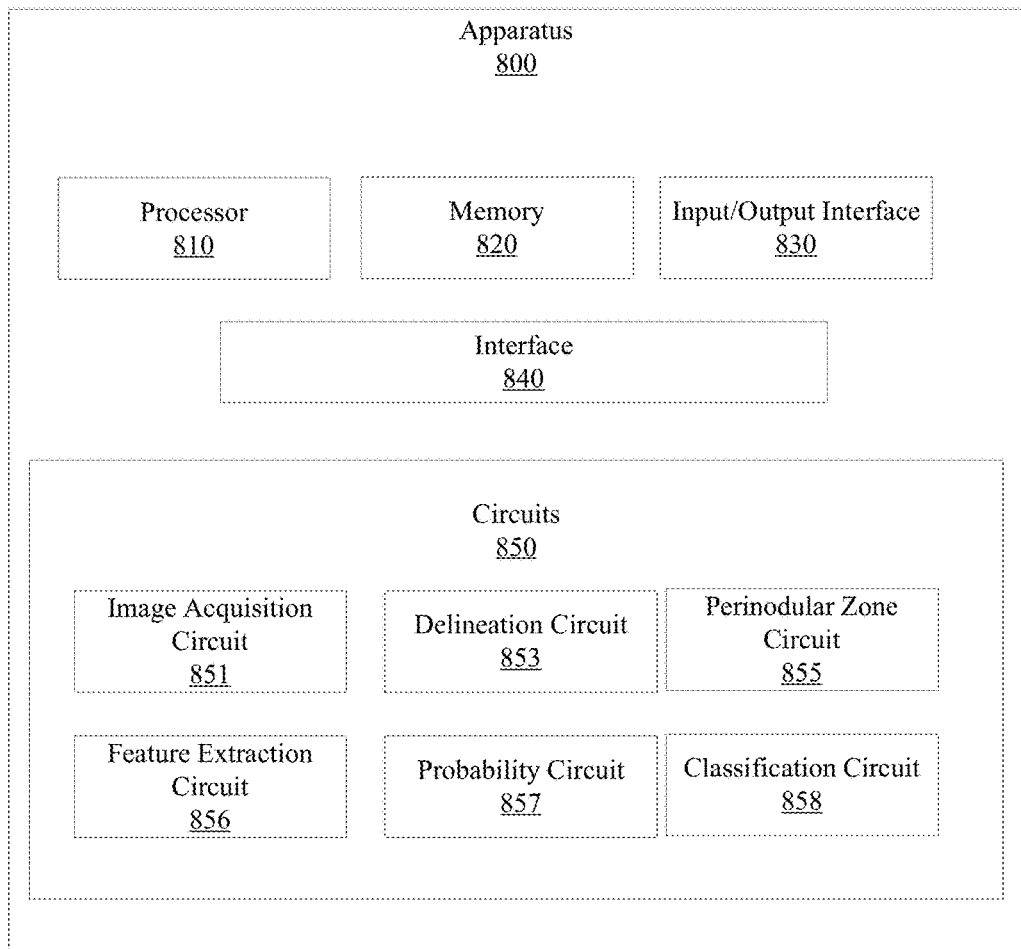
FIG. 8 illustrates an example apparatus that classifies a region of tissue in an image.

FIG. 8 illustrates an example apparatus 800 for classifying a region of tissue in an image. Apparatus 800 includes a processor 810, a memory 820, an input/output (I/O) interface 830, a set of circuits 850, and an interface 840 that connects the processor 810, the memory 820, the I/O interface 830, and the set of circuits 850. The set of circuits 850 includes an image acquisition circuit 851, a delineation circuit 853, a perinodular zone circuit 855, a feature extraction circuit 856, a probability circuit 857, and a classification circuit 858. In one embodiment, the functionality associated with the set of circuits 850 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 850 are implemented as ASICs or SOCs.

Image acquisition circuit 851 acquires an image of a region of tissue. The image may be acquired from, for example, a CT apparatus. The region of tissue may be a section of tissue demonstrating cancerous pathology in a patient. The image of the region of tissue may include an image of a nodule, a tumor, or other region of interest. In one embodiment, the image is a 1 mm to 5 mm thick, no-contrast chest CT image with a pixel size of 0.7 mm center to center. Other imaging approaches may be used to generate and access the image accessed by image acquisition circuit 851. Other image modalities, dimensions, pixel sizes, or resolutions may also be used.

Delineation circuit 853 automatically delineates the nodule, tumor, or other region of interest by distinguishing nodule tissue within the image from the background of the image. Delineation circuit 853 distinguishes nodule tissue by defining a boundary between non-nodule tissue and nodule tissue. In one embodiment, delineation circuit 853 automatically delineates the nodule using SEGvAC segmentation. In another embodiment, delineation circuit 853 automatically delineates the nodule using threshold based segmentation, deformable boundary models, active-appearance models, active shape models, graph based models including Markov random fields (MRF), min-max cut approaches, or other image delineation approaches. In one embodiment, delineation circuit 853 is configured to facilitate a human radiologist delineating the nodule. In one embodiment, delineation circuit 853 segments tumor tissue from other, non-tumor tissue in an image of a breast demonstrating cancerous pathology.

Perinodular zone circuit 855 defines a perinodular zone based, at least in part, on the nodule tissue or the nodule boundary. In one embodiment, perinodular zone circuit 855 defines the perinodular zone by defining a perinodular zone-plus-nodule region by dilating the nodule boundary a threshold amount, and subtracting the nodule region from the perinodular zone-plus-nodule region. In one embodiment, the threshold amount is within the range (4.9 mm, 7.0 mm). In another embodiment, perinodular zone circuit 855 defines the perinodular zone using other ranges or techniques. For example, perinodular zone circuit 855 may define the perinodular zone using a threshold amount within the range (3.5 mm, 5 mm) or the range (7 mm, 10 mm).

Feature extraction circuit 856 extracts a set of features from the image. The set of features includes a set of tortuosity features. Feature extraction circuit 856 identifies a vessel associated with the nodule. Feature extraction circuit 856 identifies a centerline or a branching point of the vessel associated with the nodule. Feature extraction circuit 856 circuit extracts the set of tortuosity features by segmenting a vessel from the perinodular zone using a 3D region growing approach, and by identifying a vessel center using a fast marching algorithm. Feature extraction circuit 856 computes a torsion for the segment of the vessel. Feature extraction circuit 856 also computes a curvature of a voxel of a vessel segment, where the curvature is proportional to the inverse of an osculating circle's radius. The set of tortuosity features may include the mean of torsion of a vessel segment, or the standard deviation of torsion of a vessel segment. The set of tortuosity features also may include the mean and standard deviation of the mean curvature of a group of vessel segments. The set of tortuosity features also may include the mean and standard deviation of the standard deviation of a vessel segment curvature and a total vessel segment length. The set of tortuosity features may also include branching statistics associated with the vessel. In one embodiment, feature extraction circuit 856 may also select a subset of tortuosity features from the set of tortuosity features based, at least in part, on a PCA or PCA-VIP ranking of the set of tortuosity features. The subset of tortuosity features may include at least three tortuosity features.

In one embodiment, the set of features also includes a set of texture features or a set of shape features. Feature extraction circuit 856 extracts the set of texture features or the set of shape features from the nodule tissue in the image of the delineated nodule. In one embodiment, the set of texture features includes a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, a CoLIAGe feature, or a contrast variance feature. The set of shape features may include a location feature, a size feature, a perimeter feature, an eccentricity feature, an eccentricity standard deviation, a compactness feature, a roughness feature, an elongation feature, a convexity feature, an equivalent diameter feature, a radial distance feature, an area feature, or a sphericity feature. Feature extraction circuit 856 may also select a subset of features from the set of features. Feature extraction circuit 856 may select the subset of features based on, at least in part, a PCA-VIP ranking of the set of features.

Probability circuit 857 computes a probability that the nodule tissue is benign tissue. Probability circuit 857 may compute the probability based, at least in part, on the set of tortuosity features, and the set of shape features or the set of texture features. Probability circuit 857 may also compute a probability that the nodule tissue will demonstrate a response to a treatment.

Classification circuit 858 classifies the nodule tissue based, at least in part, on the set of features or the probability. In one embodiment, classification circuit 858 classifies the nodule tissue as a benign Gr or a malignant carcinoma using an SVM classifier. The SVM classifier may be trained on a set of training features using a three-fold cross validation re-sampling approach. The set of training features may be selected using a PCA-VIP ranking of a set of features extracted from a set of training images. The set of training images may include a no-contrast CT image of a region of tissue demonstrating lung cancer pathology, granuloma secondary to histoplasmosis infection, or other pathology. In one embodiment, classification circuit 858 classifies the nodule tissue as a carcinoma or a Gr using an LDA of the subset of features or using a QDA of the subset of features.

In another embodiment, classification circuit 858 may classify the nodule tissue as another type of tissue using other analytical techniques.

In another embodiment, classification circuit 858 may control a CADx system to classify the image based, at least in part, on the classification. For example, classification circuit 858 may control a lung cancer CADx system to classify the image based, at least in part, on the set of features. In other embodiments, other types of CADx systems may be controlled, including CADx systems for distinguishing nodules among breast cancer, oral cancer, prostate cancer, colon cancer, brain cancer, rectal cancer, and other diseases where disease classification and prognosis prediction may be based on tortuosity features, textural features, or shape features quantified from CT or MRI images or other types of medical images of tissue demonstrating a pathology.

In one embodiment of apparatus 800, the set of circuits 850 also includes a display circuit. The display circuit may control the CADx system to display the classification, the nodule, the perinodular zone, the texture features, the tortuosity features, or the shape features, on a computer monitor, a smartphone display, a tablet display, or other displays. Displaying the classification or the features may also include printing the classification or the features. The display circuit may also control the CADx to display an image of the region of tissue demonstrating a nodule. The image of the region of tissue demonstrating a nodule may include a delineated or segmented representation of the nodule or vessels associated with the nodule. By displaying the features and the image of the nodule, example apparatus provide a timely and intuitive way for a human radiologist to more accurately classify pathologies demonstrated by a patient, thus improving on conventional approaches to predicting cancer recurrence and disease progression.

Figure 9:
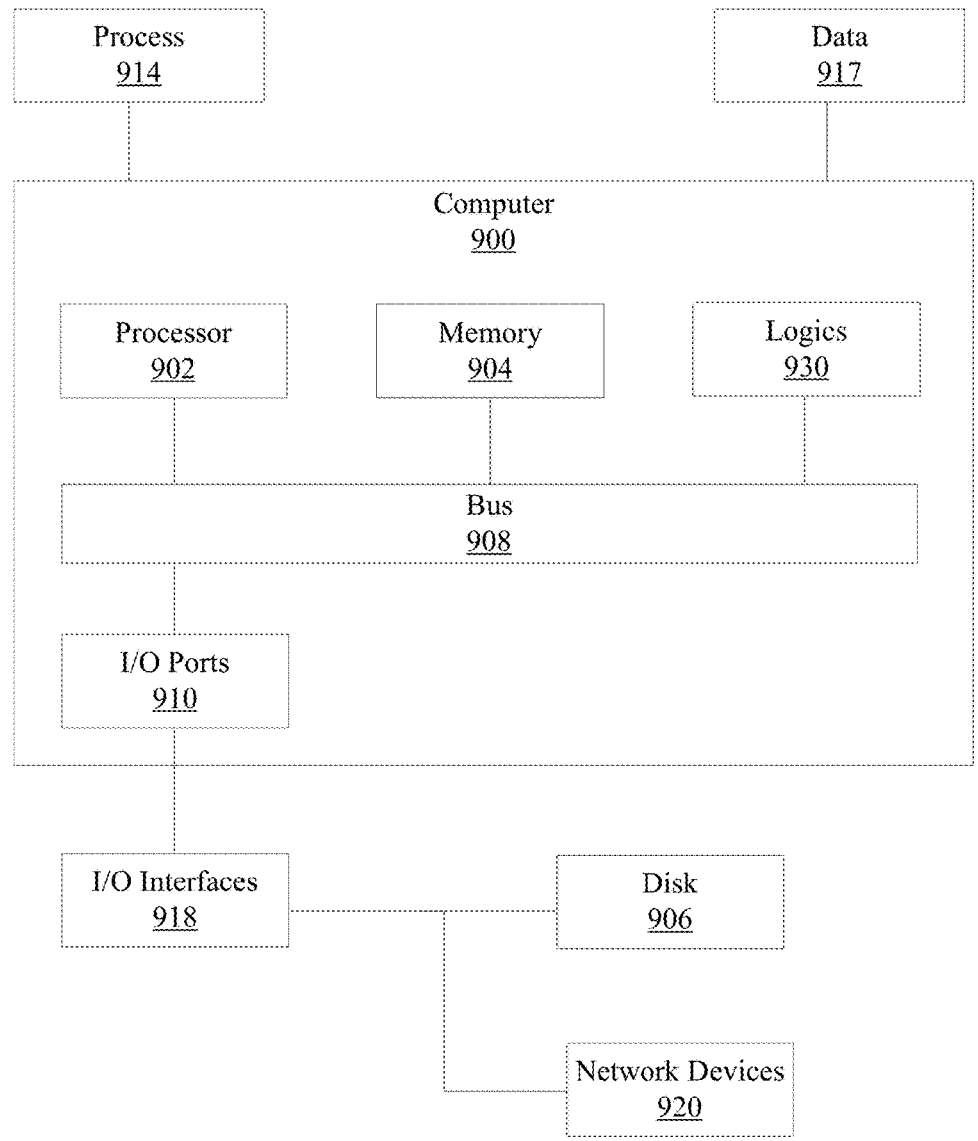
FIG. 9 illustrates an example computer in which example methods and apparatus may operate.

FIG. 9 illustrates an example computer 900 in which example methods illustrated herein can operate and in which example circuits or logics may be implemented. In different examples, computer 900 may be part of a CT system, may be operably connectable to a CT system, may be part of an MRI system, or may be part of a CADx system.

Computer 900 includes a processor 902, a memory 904, and input/output ports 910 operably connected by a bus 908. In one example, computer 900 may include a set of logics 930 that perform a method of characterizing a nodule in a region of lung tissue. Thus, the set of logics 930, whether implemented in computer 900 as hardware, firmware, software, and/or a combination thereof may provide means (e.g., hardware, software) for characterizing a nodule in a region of lung tissue. In different examples, the set of logics 930 may be permanently and/or removably attached to computer 900. In one embodiment, the functionality associated with the set of logics 930 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 930 are implemented as ASICs or SOCs.

Processor 902 can be a variety of various processors including dual microprocessor and other multi-processor architectures. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a solid state device (SSD), a flash memory card, or a memory stick. Furthermore, disk 906 may include optical drives like a CD-ROM or a digital video ROM drive (DVD ROM). Memory 904 can store processes 914 or data 917, for example. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, logics, and peripherals using other busses that are not illustrated (e.g., PCIE, SATA, Infiniband, 1394, USB, Ethernet).

Computer 900 may interact with input/output devices via I/O interfaces 918 and input/output ports 910. Input/output devices can include, but are not limited to, digital whole slide scanners, a CT machine, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a solid state device (SSD), a memory stick, a data storage device, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple circuits into one physical logic or circuit. Similarly, where a single logical circuit is described, it may be possible to distribute that single circuit between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A computer-aided diagnosis (CADx) apparatus for assigning malignancy risk to lung nodules on computed tomography (CT) imagery, the apparatus comprising:
    a memory configured to store at least one CT image of a region tissue demonstrating lung nodules, the at least one CT image including a nodule and a lung parenchyma region, where the nodule includes a boundary, and where the lung parenchyma region includes a plurality of parenchymal rings, where a member of the plurality of parenchymal rings is based on a dilation of the nodule boundary;
    a processor;
    an input/output (VO) interface;
    a set of circuits; and
    an interface that connects the memory, the processor, the VO interface, and the set of circuits, the set of circuits comprising:
        a feature extraction circuit configured to:
            automatically extract a first set of quantitative features from the nodule represented in the at least one CT image, and
            automatically extract a second set of quantitative features from the lung parenchyma region immediately surrounding the nodule represented in the at least one CT image;

a feature selection circuit configured to select an optimally predictive feature set from the first set of quantitative features and the second set of quantitative features; and a training circuit configured to train a classifier using the optimally predictive feature set to assign malignancy risk to a lung nodule represented in a CT image of a region of tissue demonstrating lung nodules.

2. The CADx apparatus of claim 1, where the first set of quantitative features includes a texture feature or a shape feature.

3. The CADx apparatus of claim 1, where the second set of quantitative features includes a texture feature or a shape feature.

4. The CADx apparatus of claim 1, where the feature selection circuit is configured to select the optimally predictive feature set using a principal component analysis variable importance of the projections (PCA-VIP) feature ranking or PCA feature ranking.

5. The CADx apparatus of claim 1, where the classifier is a machine learning classifier, and where the training circuit is configured to train the machine learning classifier using a cross-validation approach.

6. The CADx apparatus of claim 5, the set of circuits further comprising a malignancy risk assessment circuit configured to:

access a diagnostic CT image of a region of tissue demonstrating cancerous pathology;

extract a set of features from a nodule region and from an immediately surrounding lung parenchyma represented in the diagnostic CT image;

provide the set of features to the machine learning classifier;

receive, from the classifier, a risk that the region of tissue is malignant; and classify the nodule as malignant or benign based on the risk.

7. A non-transitory computer-readable storage device storing computer-executable instructions that when executed by a computer control the computer to perform a method, the method comprising:

accessing a set of development data, where the development data includes a set of three dimensional (3D) computed tomography (CT) images representing a region of tissue demonstrating lung nodules, the set of 3D CT images including a malignant subset, and a benign subset;

segmenting a nodule represented in a member of the set of 3D CT images, the segmented nodule defining a volume of interest (VOI), where the segmented nodule has a boundary;

segmenting a set of parenchymal quartile rings based on the segmented nodule, where each parenchymal quartile ring defines a VOI 3D expansion, where the set of parenchymal quartile rings is based on a dilation of the nodule boundary, where the dilation ratio is defined by a magnitude of an axis of the nodule, where the dilation ratio defines a 25% expansion, a 50% expansion, a 75% expansion, or a 100% expansion;

extracting a set of features from the segmented nodule and from the set of parenchymal quartile rings;

for each VOI 3D expansion:
selecting a set of representative features from the set of features;
selecting a set of information optimized features from the set of representative features;

training a set of candidate classifiers on the set of information optimized features to assign malignancy risk to the nodule; and selecting the best performing candidate classifier from the set of candidate classifiers.

8. The non-transitory computer-readable storage device of claim 7, where selecting the set of information optimized features from the set of representative features includes selecting the set of information optimized features using principal component analysis variable importance of the projections (PCA-VIP) feature ranking or PCA feature ranking.

9. The non-transitory computer-readable storage device of claim 7, where training the set of candidate classifiers on the set of information optimized features includes training the set of candidate classifiers using a cross-validation approach.

10. The non-transitory computer-readable storage device of claim 7, where the best performing candidate classifier is selected based on an area under the curve receiver operating characteristic (AUC-ROC) analysis of the candidate classifiers.

11. The non-transitory computer-readable storage device of claim 7, the method further comprising:

accessing a diagnostic 3D CT image of a region of tissue demonstrating cancerous pathology;

segmenting a nodule represented in the diagnostic 3D CT image;

defining a VOI based on the segmented nodule;

segmenting a set of parenchymal quartile rings based on the segmented nodule, where each parenchymal quartile ring defines a VOI 3D expansion;

extracting a set of features from the segmented nodule and from the set of parenchymal quartile rings;

providing the set of features to the best performing candidate classifier;

receiving, from the best performing candidate classifier, a malignancy risk, where the best performing candidate classifier computes the malignancy risk based on the set of features;
and classifying the nodule as malignant or benign based, at least in part, on the malignancy risk.

12. A non-transitory computer-readable storage device storing instructions that when executed control a computer-aided diagnosis (CADx) tool to perform operations, the operations comprising:

accessing a three dimensional (3D) diagnostic computed tomography (CT) image of a region of tissue demonstrating lung cancer;

segmenting a nodule represented in the 3D diagnostic CT image, the nodule having a volume of interest (VOI);

segmenting a set of parenchymal rings based on a 3D expansion of the VOI of the segmented nodule, where the set of parenchymal rings includes a plurality of parenchymal rings;

extracting a set of nodule features from the segmented nodule; extracting a set of perinodular features from the set of parenchymal rings; and computing a malignancy risk for the nodule based, at least in part, on the set of nodule features and the set of perinodular features.

13. The non-transitory computer-readable storage device of claim 12, where segmenting the nodule represented in the 3D diagnostic CT image includes segmenting the nodule using a threshold based segmentation approach, deformable boundary models, active-appearance models, active shape models, graph based models including Markov random fields (MRF), or a min-max cut approach.

14. The non-transitory computer-readable storage device of claim 12, where segmenting the nodule represented in the 3D diagnostic CT image includes segmenting the nodule using a spectral embedding gradient vector flow active contour (SEGvAC) model.

15. The non-transitory computer-readable storage device of claim 12, where the set of parenchymal rings includes a 25% expansion ring, a 50% expansion ring, a 75% expansion ring, and a 100% expansion ring.

16. The non-transitory computer-readable storage device of claim 12, where the 3D expansion of the VOI of the segmented nodule is based on a function of a property of the nodule, the nodule having a boundary.

17. The non-transitory computer-readable storage device of claim 1, where the function of the property of the nodule defines a dilation of the nodule boundary, where the dilation ratio is defined by a magnitude of an axis of the nodule.

18. The non-transitory computer-readable storage device of claim 17, where the property of the nodule includes a diameter of the nodule, a radius of the nodule, a perimeter of the nodule, an area of the nodule, a volume of the nodule, or other property of the nodule.

19. The non-transitory computer-readable storage device of claim 12, the operations further comprising classifying the nodule as malignant or benign based on the malignancy risk.

\* \* \* \* \*

UNITED STATES PATENT AND TRADEMARK OFFICE
CERTIFICATE OF CORRECTION

PATENT NO. : 10,470,734 B2
APPLICATION NO. : 16/043498
DATED : November 12, 2019
INVENTOR(S) : Madabhushi et al.

It is certified that error appears in the above-identified patent and that said Letters Patent is hereby corrected as shown below:

In the Claims

Column 20, Line 55, Claim 1: Replace "(VO)" with – (I/O) –

Column 20, Line 58, Claim 1: Replace "(VO)" with – (I/O) –

Signed and Sealed this
Twenty-fourth Day of December, 2019

Andrei Iancu
*Director of the United States Patent and Trademark Office*